US00PP27925P3

(12) United States Plant Patent
Kordes

(10) Patent No.: US PP27,925 P3
(45) Date of Patent: Apr. 25, 2017

(54) CLIMBING ROSE PLANT NAMED 'KORJOSLIO'

(50) Latin Name: *Rosa hybrida*
Varietal Denomination: KORjoslio

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop, DE (US)

( * ) Notice: Subject to any disclaimer, the term of this patent is extended or adjusted under 35 U.S.C. 154(b) by 48 days.

(21) Appl. No.: 14/756,359

(22) Filed: Sep. 1, 2015

(65) Prior Publication Data

US 2017/0064889 P1 Mar. 2, 2017

(51) Int. Cl.
*A01H 5/02* (2006.01)

(52) U.S. Cl.
USPC ..... Plt./110

(58) Field of Classification Search
USPC ..... Plt./110
See application file for complete search history.

*Primary Examiner* — Keith Robinson

(57) ABSTRACT

'KORjoslio' is a new and distinct variety of *Rosa hybrida* which is characterized by the combination of a bushy and upright growth habit with large, white, very-double flowers. The new variety propagates successfully by grafting and by stem cuttings and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORjoslio'.

BACKGROUND OF THE INVENTION

The present invention relates to a new and distinct *Rosa hybrida*, climbing rose cultivar, which has been given the variety denomination of 'KORjoslio'. Its market class is PLT/110.

Parentage: The *Rosa hybrida* variety 'KORjoslio' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORjoslio' from all other varieties known to the inventor.

'KORjoslio' is a seedling selection which resulted from the controlled pollination of *Rosa hybrida* 'KORklemol' (U.S. Plant Pat. No. 16,938), the seed parent, and an unnamed breeding line developed and owned by the same inventor, the pollen parent, during the summer of 2005.

As part of a rose development program, Tim-Hermann Kordes germinated seeds from the aforementioned hybridization during the following winter and conducted evaluations and observations on the resulting seedlings in a controlled environment in Offenseth-Sparrieshoop, Germany. The resulting seedlings exhibited distinctive physical and biological characteristics. The new rose plant was selected as a single plant in May of 2006 from the seedling beds due to its superior characteristics and asexually propagated for further evaluation. This new and distinctive rose variety was given the name 'KORjoslio'.

Asexual Reproduction: The first asexual propagation of 'KORjoslio' was performed in July of 2006 at the inventor's nursery in Offenseth-Sparrieshoop, Germany. Subsequently, 'KORjoslio' has been successfully propagated by stem cuttings and grafting in Jackson County, Oreg. These initial and other subsequent propagations conducted in controlled environments demonstrate that 'KORjoslio' reproduces true to type in successive generations of asexual reproduction.

SUMMARY OF THE INVENTION

The following characteristics have been repeatedly observed and represent the distinguishing characteristics of the new *Rosa hybrida* cultivar 'KORjoslio'. These traits, in combination, distinguish 'KORjoslio' as a new and distinct cultivar.

1. *Rosa hybrida* 'KORjoslio' exhibits an upright and climbing growth habit; and
2. *Rosa hybrida* 'KORjoslio' exhibits an abundance of flowers; and
3. *Rosa hybrida* 'KORjoslio' exhibits a very-double flower habit; and
4. *Rosa hybrida* 'KORjoslio' exhibits very strong disease resistance; and
5. *Rosa hybrida* 'KORjoslio' exhibits abundant foliage.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORjoslio', taken from plants of two years of age.

DETAILED BOTANICAL DESCRIPTION

The following is a detailed botanical description of a new and distinct variety of *Rosa hybrida* known as 'KORjoslio', based upon field observations made in June of 2015 from two year old plants, grown in-ground, at a nursery in Jackson County, Oreg.

Those skilled in the art will appreciate that certain characteristics will vary with older or, conversely, with younger plants. 'KORjoslio' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 2001 edition except where common terms of color are used.

A botanical description of 'KORjoslio' and comparisons with the parent plants and other similar varieties of *Rosa hybrida* are provided below.

General plant description:

*Growth rate*.—Vigorous.

*Growth habit*.—Upright and climbing.

*Mature dimensions*.—Approximately 200 cm tall and 100 cm wide.

*Cold hardiness*.—Grown successfully in USDA Hardiness Zones 6 through 9.

*Propagation*.—Grafting and stem cuttings.

*Disease resistance*.—Very good resistance to blackspot (*Diplocarpon rosae*) and rust (*Phragmidium* sp.) diseases under normal growing conditions in Jackson County, Oreg.

Root system: Fibrous.

Stems:

*Immature stem color*.—Yellow-Green Group 146C.

*Mature stem color*.—Yellow-Green Group 146C.

*Anthocyanin intonations*.—Greyed-Red Group 178B.

*Stem texture*.—Smooth and glaucous.

*Stem diameter*.—8 to 10 mm, on average.

*Prickles*.—Incidence — Average of 7 prickles per 10 cm of stem. Size — Average length is 7 mm. Immature prickle color — Yellow-Green Group 144C. Mature prickle color — Yellow-Green Group 154C, senescing to Grey-Brown Group 199D. Anthocyanin intonations — Greyed-Red Group 178C present on mature prickles. Shape — Deeply concave. Texture — Smooth.

Leaves:

*Arrangement*.—Imparipinnate compound leaves; mature axillary leaves consisting of 5 leaflets.

*Attachment*.—Petiolate.

*Dimensions*.—Approximately 140 to 155 mm long and 100 mm wide.

*Abundance*.—Very abundant.

*Stipules*.—Size — Approximately 25 to 30 mm long and 5 to 6 mm wide. Stipule color — Yellow-Green Group 144C. Anthocyanin intonations — Greyed-Purple Group 183A; present on stipitate glands, apex and adaxial midrib. Stipitate glands — Abundant; only present at margins. Margins — Cilliate. Texture, adaxial surface — Smooth and sparsely pubescent. Texture, adaxial surface — Smooth and sparsely pubescent. Apex — Apiculate. Base — Winged.

*Petiole*.—Length — Approximately 30 to 35 mm. Diameter — Approximately 1 to 2 mm. Petiole color, adaxial surface — Yellow-Green Group 144B. Petiole color, abaxial surface — Yellow-Green Group 144B. Margins — Entire with a limited number of stipitate glands. Anthocyanin intonations — Greyed-Purple Group 183A; present on prickles and stipitate glands. Prickles — 2 small prickles on the abaxial surface. Stipitate glands — Limited number present on margins and abaxial surface. Texture — Papillate. Strength — Somewhat strong.

*Rachis*.—Length — Approximately 20 to 25 mm. Diameter — Approximately 1 to 2 mm. Color — Yellow-Green Group 144B. Anthocyanin intonations — Greyed-Purple Group 183A; present on prickles, stipitate glands and margins. Margins — Entire with a limited number of stipitate glands. Prickles — A few small prickles underneath. Stipitate glands — Limited number present on margins and abaxial surface. Texture — Papillate.

*Leaflets*.—Quantity — Normally 5 leaflets present on leaves in middle of the stem. Dimensions — Average size of the terminal leaflet is 50 to 60 mm long and 30 to 40 mm wide. Shape — Elliptical. Apex — Acuminate. Base — Obtuse. Margins — Serrated; slight undulation present, particularly on terminal leaflet. Texture, adaxial surface — Semi-glossy and leathery. Texture, abaxial surface — Matte and leathery. Immature foliage color, adaxial surface — Yellow-Green Group 146C. Immature foliage color, abaxial surface — Yellow-Green Group 146C. Mature foliage color, adaxial surface — Yellow-Green Group 147A. Mature foliage color, abaxial surface — Yellow-Green Group 146B. Anthocyanin intonations — Greyed-Red Group 178A; present on immature foliage. Venation — Reticulate. Petiolule — Dimensions — 2 to 3 mm long and 1 mm in diameter. Petiolule color, adaxial and abaxial surfaces — Yellow-Green Group 145C. Anthocyanin intonations — Greyed-Red Group 182A present on stipitate glands. Prickles — None present. Stipitate Glands — A limited number present along margins and abaxial surface. Texture, adaxial and abaxial surfaces — Smooth and sparsely pubescent. Margins — Entire with a limited number of stipitate glands.

Inflorescence:

*Inflorescence type*.—Both corymbs with multiple flowers and solitary flowers observed.

*Blooming habit*.—Recurrent.

*Quantity of flowers*.—Generally 1 to 3 flowers on corymbs.

*Size*.—Corymbs are 90 mm tall and 120 mm wide, on average.

*Peduncle*.—Surface — Glabrous with a limited number of stipitate glands, occasionally present. Length — 15 to 75 mm average length. Diameter — 3 to 4 mm average diameter. Color — Yellow-Green Group 145A. Anthocyanin intonations — Greyed-Red Group 182A. Strength — Somewhat strong. Texture — Glabrous to papillate.

Flowering laterals: Present below the initiation of inflorescence. Generally 3 to 4 flowering laterals are present, with 7 flowers per flowering shoot.

Bud:

*Bud form*.—Long, ovoid; high centered.

*Size*.—Upon opening, 30 to 35 mm in length from base of receptacle to distal end of bud and 20 to 30 mm diameter at its widest point.

*Texture*.—Leathery.

*Color, as sepals first unfold*.—White Group 155B, with intonations of Yellow-Green Group 145C.

*Color when one-quarter open, inner and outer surfaces*.—Marginal zone — White Group 155B. Middle zone — White Group 155B. Basal zone — Yellow-Green Group 145C.

Flower:

*Pedicel*.—Surface — Glabrous with an abundance of stipitate glands. Length — Ranging from 50 to 100 mm. Diameter — 2.5 to 3 mm, on average. Color — Yellow-Green Group 145A. Anthocyanin intonations — Greyed-Red Group 178A. Strength — Somewhat weak. Texture — Papillate.

*Sepals*.—Diameter of calyx — 50 mm, at anthesis. Quantity — Five. Color, adaxial surface — Yellow-Green Group 147C. Color, abaxial surface — Yellow-Green Group 144A. Anthocyanin intonations — Greyed-Red Group 182A. Dimensions — 25 mm long and 7 mm wide, on average. Shape — Weak foliaceous appendages on 3 of the 5 sepals. Apex — Apiculate. Base — Flat at union with receptacle. Texture, adaxial surface — Smooth and hoary. Texture, abaxial surface — Leathery. Margins — Entire and cilliate margins observed. Stipitate glands — Abundant; at and near margins.

*Corolla*.—General shape of corolla — Rosette; round. Shape of corolla when viewed from the side — Upon opening, upper portion — Convex. Upon opening, lower portion — Concave. Open flower, upper portion — Flat. Open flower, lower portion — Concave. Aspect — Slightly pendulous. Dimensions — Medium-sized corolla for a climbing rose. When open, the flower diameter is 70 to 80 mm and the flower height is 45 mm from the top of the bloom to the base of the receptacle. Fragrance — Moderate. Duration — On the plant 4 days. Senesced petals drop away cleanly. Petals — Petal arrangement — Not formal. Petal count — Exhibits very-double flowers with approximately 80 petals under normal conditions. Petal reflex — Strong; double reflex. Petal reflex occurs one by one. Petal margin — Typically entire; some innermost petals ruffled. Petal shape — Obovate. Apex — Obtuse. Base — Cuneate. Dimensions — Approximately 22 to 40 mm long and 17 to 40 mm wide. Texture, inner surface — Smooth. Texture, outer surface — Smooth. Petal color, upon opening — Outermost petals, inner and outer surfaces — Marginal zone — White Group 155C, with occasional intonations of Red-Purple Group N66C. Middle zone — White Group 155C. Basal zone — Yellow-Green Group 145C. Innermost petals, inner and outer surfaces — White Group 155C. Basal petal spots, upon opening — Basal petal spot, outermost petals — None observed. Basal petal spot, innermost petals — Dimensions — 2 mm high and 1 mm wide, on average. Outer surface — Yellow Group 3C. Inner surface — Yellow Group 3C. Petal color, after opening — Outermost petals, inner and outer surfaces — White Group 155C, with occasional intonations of Red-Purple Group N66C. Innermost petals, inner and outer surfaces — White Group 155C. Basal petal spots, after opening — No distinctive basal coloration. General Tonality — White Group 155D, at anthesis, and fading to White Group 155B after 3 days.

*Petaloids*.—Quantity — 15 petaloids per flower, on average. Dimensions — Approximately 12 to 22 mm long and 16 to 17 mm wide. Color, inner and outer surfaces — Marginal zone — White Group 155C. Middle zone — White Group 155C. Basal zone — White Group 155C. Margins — Undulated. Shape — Spatulate. Apex — Obtuse. Base — Cuneate. Texture, inner and outer surfaces — Smooth.

Reproductive organs:

*Stamens*.—Quantity — Approximately 60, on average, and regularly arranged around the styles. Anthers — Dimensions — Approximately 1.5 to 2 mm long and 1.5 to 2 mm wide. Color — Yellow-Orange Group 14D. Pollen — Generally present; medium density. Pollen Color — Greyed-Orange Group N163D. Filaments — Color — Yellow Group 12A. Length — 5 to 7 mm.

*Pistils*.—Quantity — Few; approximately 50 present. Stigmas — Dimensions — 1 mm long and 1 mm wide. Location — Slightly superior or equal to anthers. Color — Yellow Group 3D. Styles — Length — Approximately 5 to 9 mm long. Color — White Group 155A, with intonations of Red Group 52A.

*Ovary*.—Dimensions — Approximately 2 to 3 mm long and 1 to 2 mm in diameter. Color — White Group 155A.

*Receptacle*.—Shape — Funnel-shaped. Dimensions — Approximately 7 mm high and 11 mm wide. Surface — Glaucous. Color — Yellow-Green Group 144B, with intonations of Greyed-Red Group 178A. Texture — Glabrous.

Hips and seed formation: Not observed.

Comparisons with the Parents

The new rose plant may be distinguished from its seed parent, *Rosa hybrida* 'KORklemol', by the following combination of characteristics:

1. 'KORjoslio' exhibits a white flower color, whereas 'KORklemol' exhibits yellow flowers with pink edges.
2. 'KORjoslio' exhibits very-double flowers with approximately 80 petals, whereas 'KORklemol' exhibits double flowers with approximately 20 to 25 petals.
3. 'KORjoslio' exhibits a moderate degree of plant vigor, whereas 'KORklemol' exhibits a high degree of plant vigor.

The new rose plant may be distinguished from its pollen parent, an unnamed seedling, by the following combination of characteristics:

1. 'KORjoslio' exhibits a white flower color, whereas the pollen parent exhibits a cream flower color.
2. 'KORjoslio' exhibits large flowers for a rose of this type, whereas the flowers of the pollen parent are of a medium size for a climbing rose.

3. 'KORjoslio' exhibits a climbing habit with dense and bushy foliage, whereas the pollen parent exhibits an arching growth habit with a limited amount of foliage.

Comparisons with Similar *Rosa hybrida* Cultivars Known to the Inventor

For a comparison, several physical characteristics of the rose variety 'KORhemtra', a rose variety from the same inventor described and illustrated in U.S. patent application Ser. No. 13/987,681 are compared to 'KORjoslio' in Chart 1.

CHART 1

| Characteristic | 'KORjoslio' | 'KORhemtra' |
|---|---|---|
| Petal count. | Approximately 80 petals under normal conditions. | Approximately 50 petals under normal conditions. |
| Typical number of leaflets per leaf. | Typically 5 leaflets on mature axillary leaves. | Typically 7 leaflets on mature axillary leaves. |
| Length of leaves. | 140 to 155 mm. | 175 to 185 mm. |

That which is claimed:

1. A new and distinct variety of rose plant named 'KORjoslio', as described and illustrated herein.

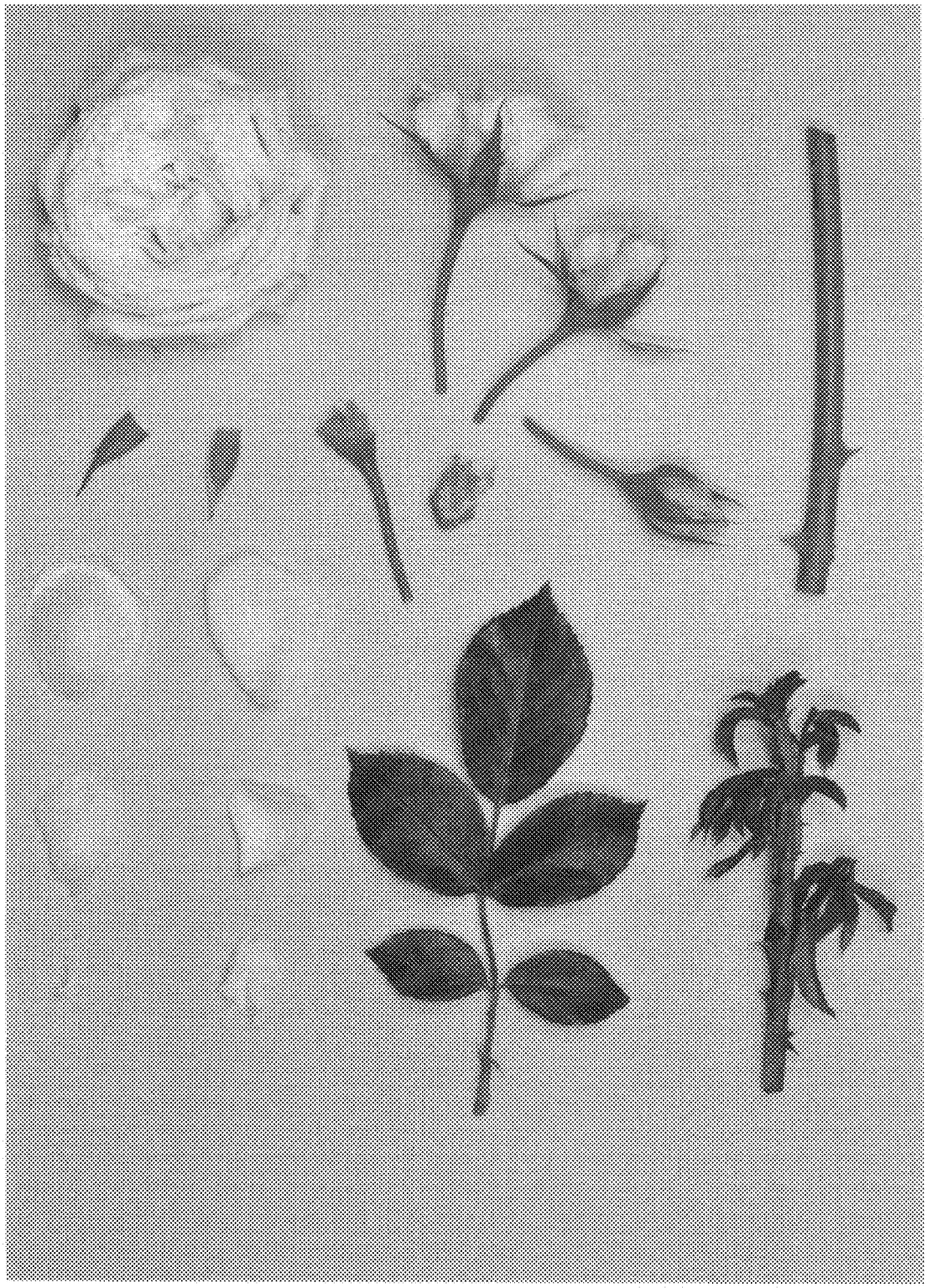

* * * * *